United States Patent [19]

Misch

[11] 4,382,791
[45] May 10, 1983

[54] INTRAMUCOSAL INSERT AND METHOD OF RETAINING A DENTURE UTILIZING THE SAME

[76] Inventor: Carl E. Misch, 1611 Monroe, Dearborn, Mich. 48124

[21] Appl. No.: 336,568

[22] Filed: Jan. 4, 1982

[51] Int. Cl.³ .............................................. A61C 8/00
[52] U.S. Cl. .................................... 433/172; 433/173
[58] Field of Search ............................... 433/172, 173

[56] References Cited

U.S. PATENT DOCUMENTS 2,374,422  4/1945  Dahl ................................. 433/173
3,905,108  9/1975  Weiss et al. ...................... 433/173

Primary Examiner—Robert Peshock
Attorney, Agent, or Firm—Basile, Weintraub & Hanlon

[57] ABSTRACT

An intramucosal insert and method of retaining a denture utilizing the same. The intramucosal insert comprises a metallic projection having a dome-shaped head adapted to be seated within the mucosal tissue surrounding the jawbone of a patient, a planar base having top and bottom surfaces and contiguous side edges and an elongated neck having a cross section narrower than the cross section of the head connecting the head and the base. In utilizing the intramucosal insert, the base is secured in position in the denture, with the neck and head portions projecting outward therefrom. An elongated bore is formed in a mucosal tissue having a diameter proximate the cross-section of the neck of the insert. An enlarged cavity is formed at the interior end of the bore in the mucosal tissue having a shape proximate the shape of the head of the insert with a bottom surface extending outward from the sides of the bore to define a seat for the bottom surface of the head of the insert.

3 Claims, 3 Drawing Figures

INTRAMUCOSAL INSERT AND METHOD OF RETAINING A DENTURE UTILIZING THE SAME

BACKGROUND OF THE INVENTION

1. Field of the Invention

This invention relates, in general, to dentures and, more specifically, to inserts for retaining a denture in the mucosal tissue of a patient.

2. Description of the Prior Art

Millions of people today require full or partial dentures to replace missing teeth. With a partial denture, the denture can be securely anchored to the surrounding teeth for full retention.

However, when a full denture is required, anchoring the denture to surrounding teeth is not possible and other securing or anchoring means must be employed. A common retention means is the use of an adhesive to hold the denture in place on the mucosal tissue of the mouth. However, such adhesives have not been fully effective in creating a stable and secure mounting of the denture and commonly result in movement and/or slippage of the denture.

Another means for securely retaining a denture in position which is finding widespread use today is the use of an intermucosal insert. As shown in U.S. Pat. No. 3,905,108, the insert is a small metallic projection having a base, an elongated neck and a mushroom-shaped head. The base of the insert is mounted in a cavity on the denture and is held in place by an adhesive, such as acrylic cement. The neck and head of the insert project outward from the denture and are adapted to be inserted into a suitably formed cavity in the mucosal tissue surrounding the jawbone of a patient. After insertion of the insert into the cavity, the surrounding mucosal tissue heals and grows around the neck and head of the insert within a short period of time to form a secure and resilient socket for the insert.

However, the use of such previously devised intramucosal inserts has not been without problems. Such inserts are mounted in the denture by means of an acrylic cement which requires several hours to harden thereby prolonging the construction time of the denture. Furthermore, despite precautions such as the use of a plastic sleeve surrounding the neck of the insert, etc., excess acrylic cement invariably is deposited on the upper surface of the base of the insert and on the denture thereby requiring time-consuming cleaning and grinding operations to remove the excess cement so as to provide a smooth surface on the denture which would not irritate the adjoining mucosal tissue.

Another problem encountered with the use of such inserts involves the formation of a cavity in the mucosal tissue for receiving the neck and head of the insert. The position of the cavity is difficult to accurately establish since a plurality, typically fourteen, inserts are employed in a full upper or lower denture. The inserts are arranged in two offset rows on either side of the palatial slope and the ridge crest of the denture. The inserts are secured in position on the denture prior to the preparation of the receptor cavities in the mucosal tissue. This often results in mis-positioning of the receptor cavity and causes misalignment of the inserts when the inserts are inserted into the mouth of the patient. During such installation, the palatial inserts slide along the ridge and do not fully seat within the palatial receptor cavities thereby resulting in a misfit of the denture and less than full retention.

Finally, the receptor cavitites in the mucosal tissue are formed by using a burr which forms an elongated, cylindrical cavity within the mucosal tissue. The cavity has a diameter only slightly smaller than the width of the head of the insert such that the head of the insert is slidably inserted into the cavity in a snug fashion prior to regrowth of the surrounding tissue around the neck and head of the insert. However, due to the resilient nature of the mucosal tissue, the tissue tends to force the insert out of the cavity before the tissue can fully regrow around the insert thereby resulting in a partial disengagement of the insert from the cavity and a resultant poor fit of the denture on the tissue.

Further, as the cavity is formed with a diameter approximately equal to the diameter of the head of the insert, a large space is created between the sides of the cavity and the much narrower diameter of the neck of the insert. This has prevented the tissue from forming a solid cuff completely around the neck of the insert and, in some cases, has resulted in complete non-adhesion of the tissue to the neck of the insert.

Thus, it would be desirable to provide an intramucosal insert which overcomes the problems of previously devised intramucosal inserts in providing a secure retention of a denture on the mucosal tissue of a patient. It would also be desirable to provide an intramucosal insert which is able to be more securely retained within the mucosal tissue. It would also be desirable to provide an intramucosal insert which may be mounted on the denture in a simple and quick manner. Finally, it would be desirable to provide an intramucosal insert and method for retaining a denture on the mucosal tissue of a patient which provides a more secure retention of the denture on the tissue.

SUMMARY OF THE INVENTION

There is disclosed herein a unique intramucosal insert for retaining a denture in position on the mucosal tissue surrounding the jawbone of a patient. The insert comprises a metallic projection having a dome-shaped head adapted to be seated within the mucosal tissue, a planar base having top and bottom surfaces and contiguous side edges and an elongated neck having a cross section narrower of the cross section of the head which connects the head and the base.

The unique intramucosal insert of the present invention overcomes many of the problems encountered with the use of previously devised intramucosal inserts. The planar base of the insert has contiguous side edges which enables the insert to be precisely mounted within the denture and prevents excess adhesive which is used to secure the insert in place on the denture from building up on the neck of the insert or on the top surface of the denture. This eliminates the previously required time-consuming adhesive removal operations. In addition, the elongated neck of the insert of the present invention allows more tissue to be contained between the head and base of the insert then with previously devised inserts which enables greater retention of the insert within the mucosal tissue. Finally, the smooth, dome-shaped head of the insert eliminates any tissue irritation when the surrounding tissue regrows around the insert.

Also disclosed is a unique method of retaining a denture in place in the mucosal tissue of a patient utilizing the intramucosal insert described above. By this method, a first elongated bore is formed in the mucosal tissue surrounding the jawbone of a patient. The first bore has a diameter proximate the cross section of the neck of the intramucosal insert. A second enlarged cavity is formed at an interior end of the first bore in the mucosal tissue and has a shape proximate the shape of the head of the insert. The cavity thus forms an interior shoulder at the end of the first bore which is adapted to form a seat for the bottom surface of the head of the insert. The shoulder prevents the tissue from urging the insert out of the cavity before the tissue regrows around the insert. In addition, the much narrower diameter of the first bore compared to the cross section of the cavity at the end thereof, which is sized to be only slightly larger then the cross section of the neck of the insert, significantly reduces the space between the neck of the insert and the sides of the cavity formed in the mucosal tissue which thereby enables the tissue to quickly regrow around the insert and form a solid adhesion bond therebetween. This affords a much quicker adhesion of the insert within the mucosal tissue and provides enhanced retention of the denture.

Finally, the unique method for retaining a denture in the mucosal tissue surrounding the jawbone of a patient also includes steps which provide placement of the receptor cavities within the mucosal tissue of the patient. According to this method, prior to the securement of the base of the insert within the denture, a transferrable indicia, such as a dye, is placed within the cavities formed on the denture and the denture is emplaced within the mouth of the patient in the desired position on the mucosal tissue. The indicia transfers to the mucosal tissue and, when the denture is removed, provides an indication of the exact position for the receptor cavities such that the inserts and cavities may be precisely aligned. This leads to enhanced retention of the denture in the mucosal tissue and provides less discomfort for the patient.

BRIEF DESCRIPTION OF THE DRAWING

The various features, advantages and other uses of the present invention will become more apparent by referring to the following detailed description and drawing in which.

DESCRIPTION OF THE PREFERRED EMBODIMENTS

Figure 1:
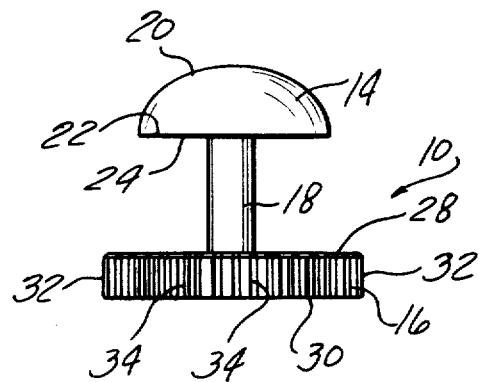
FIG. 1 is an elevational view of an intramucosal insert constructed in accordance with the teachings of the present invention.

Throughout the following description and drawing, identical reference numbers are used to refer to the same component shown in multiple figures of the drawing.

Figure 2:
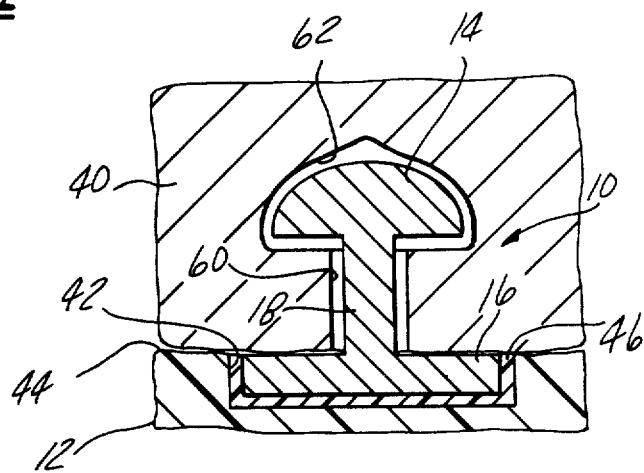
FIG. 2 is a cross sectional view illustrating the emplacement of the intramucosal insert of the present invention within a denture and the mucosal tissue of a patient.
Figure 3:
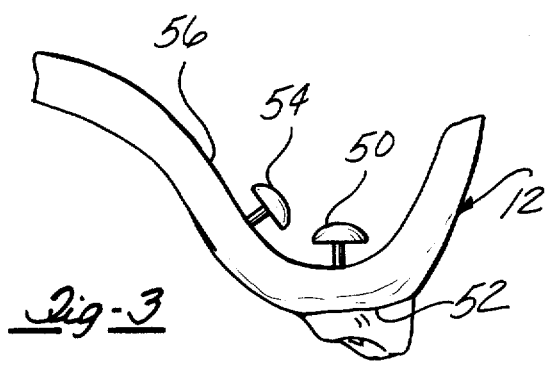
FIG. 3 is an elevational view of a denture having a plurality of intramucosal inserts of the present invention mounted therein.

Referring now to the drawing, and to FIGS. 1, 2 and 3, there is illustrated an intramucosal insert 10 which is used to retain a denture on the mucosal tissue of a patient. The intramucosal insert 10 of the present invention is adapted for securing a full conventionally formed denture, such as denture 12, shown in FIG. 3, to the mucosal tissue surrounding either of a patient's upper or lower jawbones.

As shown in FIG. 1, the intramucosal insert 10 comprises a head 14, a planar base 16 and an elongated neck 18 connecting the head 14 and the base 16.

The head 14 of the insert 10 has a dome-shaped convex configuration which presents a smooth upper surface 20. The lower or bottom surface 22 of the head 14 of the insert 10 defines a planar form which creates a shoulder 24 which provides greater retention of the insert 10 in the mucosal tissue, as described in greater detail hereafter.

The base 16 is substantially planar in form and has top and bottom flat surfaces 28 and 30, respectively. The base 16 also has a contiguous depending side edge 32 extending between the top and bottom surfaces 28 and 30 to define a solid form. As illustrated in FIG. 1, the base 16 has a larger cross section or diameter than the corresponding cross section or diameter of the head 14 of the insert 10 for reasons which will be described in greater detail hereafter.

To aid in retaining the insert 10 within the mucosal tissue of the patient, a plurality of shallow grooves or slots 34 are formed along the side edge 32 of the base 16 around the periphery of the insert 10. The grooves 34 provide additional surface area on the base 16 for receiving a suitable adhesive, as described hereafter, for retaining the base 16 of the insert 10 within the denture.

Finally, the intramucosal insert 10 of the present invention includes a neck portion 18. The neck is elongated in form and has a substantially cylindrical shape with the circular cross section. As shown in FIGS. 1 and 2, the neck 18 has a much narrower diameter or cross section then the corresponding cross section or diameter of the head 14.

The insert 10 is formed of a metallic material, such as titanium vitallium or stainless steel, for strength and resistance to deterioration over long period of use.

Referring now to FIGS. 2 and 3, the utilization of the intamucosal insert 10 described above for retaining a denture 12 in position on the mucosal tissue 40 surrounding the jawbone of a patient, will now be described. The first step in the method of retaining a denture 12 in the mucosal tissue 40 of a patient utilizing the insert 10 of the present invention is to form a suitable cavity in the denture 12 for receiving the base 16 of the insert 10. The cavity, such as cavity 42 shown in FIG. 2, has a diameter only slightly larger then the diameter of the base 16 of the insert 10 and a depth slightly larger then the height of the base 16 such that when the base 16 is disposed therein, the upper surface 28 of the base 16 will be disposed in a substantially flush arrangement with the top surface 44 of the denture 12.

The base 16 of the insert 10 is secured in position within the cavity 42 by means of a suitable adhesive 46. Preferably, the adhesive 46 comprises ethyl cyanoacrylate cement which is poured into the cavity 42 prior to insertion of the base 16 of the insert 10 thereinto. The ethyl cyanoacrylate cement quickly hardens to a dry state to securely retain the base 16 of the insert 10 in position within the denture 40, with the neck 18 and head 14 of the insert 10 extending outward therefrom.

As is conventional, a plurality of inserts 10 are utilized on a full denture to provide secure retention of the denture within the mucosal tissue surrounding the jawbone of the patient. Ideally, fourteen inserts are utilized, seven on each side of the denture. The inserts on each side are arranged in two offset rows, with four inserts, such as insert 50 shown in FIG. 3, arranged in a spaced alignment along the ridge crest 52 of the denture 12. The inserts, such as insert 50, are spaced apart at least the width of one insert along each ridge crest 52. Three inserts, such as insert 54, are disposed along the palatial slope 56 of the denture 12. The palatial inserts 54 are offset between the ridge crest inserts 50 to provide an interlocking mechanical retention for the denture 12 in the mucosal tissue.

Once the cavities 42 have been formed in the desired locations in the denture 12 and prior to the placement of the inserts 10 within such cavities 42, the upper surface of the denture 12 preferably around the cavities 42 is covered with a transferrable indicia, not shown. Preferably, the indicia is in the form of a tissue marking dye. The denture 12 is then placed in the proper position on the mucosal tissue of the patient such that the indicia is transferrable to the mucosal tissue to thereby indicate the proper location for the corresponding cavities to be formed in the mucosal tissue which receive the neck and head portions of the inserts. This proper positioning of the cavities in the mucosal tissue is critical due to the offset alignment of the ridge and palatial mounted inserts in the denture 12.

Once the locations for the cavities in the mucosal tissue have been located, the next step in the method of retaining a denture in such mucosal tissue is to form the cavities in the mucosal tissue. Each cavity in the mucosal tissue is formed in a first elongated bore 60, as shown in FIG. 2. The first bore 60 is formed by means of an elongated, straight tissue burr which is inserted into the exact center of each indicated cavity site on the mucosal tissue. The first bore 60 has a narrow diameter or cross section slightly larger then the corresponding cross section of the neck 18 of the inserts 10. In addition, the bore 60 has a length slightly shorter then the length of the neck portion 18 of the insert 10.

After the first bore 60 has been formed in the indicated location in the mucosal tissue, a second, round tissue burr is inserted through the first burr 60 and rotated to form an enlarged cavity of cul-de-sac 62 at the interior end of the first bore 60. The interior cavity 62 has a shape corresponding to the shape of the round tissue burr and, as shown in FIG. 2, is proximate or slightly larger then the shape and configuration of the head 14 of the insert 10.

The first bore 60 and interior cavity 62 thus form a receptor cavity in the mucosal tissue 40 which has a shape slightly larger then a corresponding shape of the neck 18 and head portion 14 of the insert 10. Thus, when the denture 12 is emplaced on the mucosal tissue, the head 14 and neck 18 of each insert 10 will engage a receptor cavity such that the head 14 of each insert 10 will be located within the enlarged interior cavity 62 and the neck 18 of each insert 10 will be disposed within the first bore 60 in close proximity to the side walls thereof. This affords quicker healing of the surrounding mucosal tissue which, when such tissue regrows, will form a secure adhesion to the head 14 and neck 18 of the insert 10 to securely retain the inserts 10 and the denture 12 secured thereto in position on the mucosal tissue of the patient.

Thus, there has been disclosed a unique intramucosal insert and a method for retaining a denture utilizing the same. The intramucosal insert of the present invention overcomes many of the problems encountered with the use of previously devised intramucosal inserts insofar as providing a secure retention of the denture on the mucosal tissue. Furthermore, due to the unique configuration of the intramucosal insert of the present invention, its emplacement on the denture is simplified thereby significantly reducing the amount of time and effort required to form the complete denture and mount the inserts in the desired locations therein.

The unique method for retaining a denture on the mucosal tissue which utilizes the unique intramucosal insert of the present invention uniquely ensures a secure retention of the denture. In addition, by utilizing a transferrable indicia means, such as a dye, the precise locations of the receptor cavities in the mucosal tissue can be easily ascertained to thereby provide exact and accurate alignment of such receptor cavities with the corresponding portions of the inserts secured in the denture.

What is claimed is:

1. An intramucosal insert for securing a denture in the mucosal tissue surrounding the jawbone of a patient comprising:
   a dome-shaped head adapted to be seated within the mucosal tissue;
   a planar base having top and bottom surfaces and contiguous side edges;
   a plurality of grooves formed in the side edges of the base extending between the top and bottom surfaces of the base; and
   an elongated neck having a cross section narrower than the cross section of the head connecting the head and the base.

2. A method for securing a denture in the mucosal tissue surrounding the jawbone of a patient comprising the steps of:
   forming a cavity in the denture;
   depositing an ethyl cyanoacrylate cement in the cavity;
   securing an instramucosal insert having a dome-shaped head, a planar base having top and bottom surfaces and contiguous side edges and an elongated neck having a cross section narrower than the cross section of the head connecting the head and the base in the denture in the cavity formed in the denture;
   forming a first, elongated bore in the mucosal tissue having a diameter proximate the diameter of the neck of the insert;
   forming an enlarged cavity at the interior end of the first bore in the mucosal tissue having a shape proximate the shape of the head of the insert with a bottom surface of the cavity extending outward from the side edges of the first bore to define a seat for the bottom surface of the head of the insert; and
   inserting the head and neck of the insert into the first bore and cavity until the head seats within the cavity to secure the denture in the mucosal tissue.

3. The method of claim 2 further including:
   disposing a transferrable indicia means around the cavity forming in the denture prior to emplacement of the insert therein;
   placing the denture in position on the mucosal tissue such that the indicia means is transferred to the mucosal tissue to indicate the proper location of the first bore; and
   forming the first bore at the indicated position in the mucosal tissue.

* * * * *